United States Patent [19]
Maki et al.

[11] Patent Number: 5,276,193
[45] Date of Patent: Jan. 4, 1994

[54] PROCESS FOR PREPARING N-ALKYL-SUBSTITUTED AMINOPHENOLS

[75] Inventors: Hiroshi Maki; Michihiro Kawasaki; Hiroshi Shimizu; Yoshiaki Ito, all of Chiba, Japan

[73] Assignee: Sumitomo Chemical Co., Ltd., Osaka, Japan

[21] Appl. No.: 561,419

[22] Filed: Aug. 1, 1990

[30] Foreign Application Priority Data

Aug. 1, 1989 [JP] Japan ............... 1-201031

[51] Int. Cl.⁵ ............................................ C07C 209/26
[52] U.S. Cl. .................................. 564/397; 564/395; 564/396; 564/398
[58] Field of Search ................ 564/397, 396, 398, 395

[56] References Cited

U.S. PATENT DOCUMENTS

| | | | |
|---|---|---|---|
| 2,380,420 | 7/1945 | Emerson | 564/397 |
| 2,776,313 | 1/1957 | Lappin | 260/574 |
| 4,233,448 | 11/1980 | Bright et al. | 562/458 |
| 4,233,458 | 11/1980 | Bright et al. | 562/458 |
| 4,713,488 | 12/1987 | Omatsu et al. | 564/397 |

FOREIGN PATENT DOCUMENTS

| | | |
|---|---|---|
| 0181505 | 5/1986 | European Pat. Off. . |
| 0287277 | 10/1988 | European Pat. Off. . |
| 2438506 | 2/1976 | Fed. Rep. of Germany ...... 564/397 |
| 51-19732 | 2/1976 | Japan . |
| 55-20773 | 2/1980 | Japan . |
| 61-10051 | 5/1986 | Japan . |

*Primary Examiner*—Glennon H. Hollrah
*Assistant Examiner*—Shailendra Kumar
*Attorney, Agent, or Firm*—Sughrue, Mion, Zinn, Macpeak & Seas

[57] ABSTRACT

A process for preparing an N-alkyl-substituted aminophenol is disclosed, comprising continuously feeding an aldehyde or a ketone to a reaction system containing an organic solvent, a catalyst for reduction, hydrogen, and an aminophenol to conduct a reductive alkylation reaction, wherein said reductive alkylation reaction is carried out while continuously adding an organic carboxylic acid into the reaction system. The process attains a high yield even when the catalyst is repeatedly used and does not cause corrosion of equipment.

4 Claims, No Drawings

PROCESS FOR PREPARING N-ALKYL-SUBSTITUTED AMINOPHENOLS

FIELD OF THE INVENTION

This invention relates to a process for preparing an N-alkyl-substituted aminophenol by reacting an aminophenol with an aldehyde or a ketone in the presence of an organic solvent, a catalyst for reduction, and hydrogen.

BACKGROUND OF THE INVENTION

N-Alkyl-substituted aminophenols are of extreme importance in industry as intermediates for heat-sensitive or pressure-sensitive dyes, xanthene dyes, fluorescent dyes, etc.

It is conventionally known to prepare an N-alkyl-substituted aminophenol by reductive alkylation of an aminophenol, which is carried out by continuously feeding an aldehyde or a ketone to a reaction system containing an aminophenol, an organic solvent, a catalyst for reduction, and hydrogen.

However, the conventional processes have the following disadvantages.

Catalysts for reduction generally used in reductive alkylation are noble metal catalysts, e.g., platinum metal catalysts and palladium metal catalysts. These catalysts, when used on an industrial scale, should be used repeatedly because of their expensiveness. However, where a catalyst recovered by filtration of the reductive alkylation reaction mixture is reused in the next reductive alkylation reaction, the catalyst exhibits seriously reduced performance, causing various troubles for use in industry. That is, the rate of reaction is low, which reduces productivity; the main reaction is suppressed and, instead, the aminophenol and the aldehyde or ketone are condensed to form heavy matter; and the aldehyde or ketone is reduced to increase by-production of an alcohol.

For the purpose of preventing reduction in reaction efficiency due to reduced performance of the catalyst, various proposals have hitherto been made.

For example, JP-A-55-100344 discloses a process for exchanging a half of the recovered catalyst with a fresh catalyst (the term "JP-A" as used herein means an "unexamined published Japanese patent application"). This process, however, still requires a large quantity of a fresh catalyst to be added and, hence, is not deemed to establish substantial repeated use of a catalyst for reduction.

JP-A-57-81444 discloses a process in which the amount of an aldehyde to be fed to a reaction system is adjusted to a stoichiometric amount. This process, however, is not always regarded industrially advantageous because, when applied to the production of N-alkyl-substituted aminophenols, too a low amount of the aldehyde fails to make a conversion of the aminophenol, an expensive raw material, nearly 100%. Further, since the rate of reaction becomes low in the latter half of the reaction, the reaction time should be lengthened accordingly.

Further, JP-A-55-20773 discloses a process for preparing N,N-dimethylaminobenzoic acid, in which a spent catalyst for reduction which is recovered from the reaction mixture by filtration is washed with methanol for reuse. This technique, however, is unsuitable for practical use because, as mentioned in the working examples, the reaction time becomes longer each time the recovered and methanol-washed catalyst is reused. Where the process is applied to the preparation of N-alkyl-substituted aminophenols, the reaction system suffers from an increase of a condensation reaction between an aminophenol and an aldehyde or a ketone to form heavy matter, or of a side reaction of an aldehyde or ketone to form an alcohol, thus resulting in remarkable reduction in yield of the desired N-alkyl-substituted aminophenol.

In the light of the above, these conventional techniques are not yet satisfactory from the industrial viewpoint.

It has also been suggested to add a small amount of acetic acid to the reaction system to produce an effect of keeping the catalyst surface clean against contamination as described in JP-A-55-20773. In this process, however, the whole amount of acetic acid is added before commencement of the reaction as described in the working examples. If such a manner is applied to the reaction of aminophenols, a Schiff base of an aminophenol which is very labile and ready to be condensed to form heavy matter undergoes further condensation by the action of the acetic acid added in the initial stage of the reaction, failing to improve the yield of the desired product. This phenomenon is particularly conspicuous when the catalyst is repeatedly used.

JP-A-61-100551 teaches of conduct the reaction under acidic conditions. According to the working examples thereof, since hydrogen in the nascent state is employed, a large quantity of, e.g., hydrochloric acid or acetic acid, should be used, or the reaction with hydrogen in the presence of a catalyst for reduction should be carried out in an acetic acid solvent. If this technique is adopted to the reaction of aminophenols, there is observed reduction in yield due to condensation of a Schiff base of an aminophenol to form heavy matter, and the yield of the desired product attained is very low. Besides, from the industrial standpoint, use of a large quantity of an acid gives rise to a problem of corrosion of equipment.

JP-A-51-19732 discloses a process comprising forming a Schiff base in the presence of a trace amount of an organic carboxylic acid, followed by hydrogenation. This process cannot be applied to the reaction of aminophenols because the Schiff base of aminophenol is very labile.

SUMMARY OF THE INVENTION

An object of this invention is to eliminate the disadvantages associated with the above-described conventional techniques and to provide a process for preparing an N-alkyl-substituted aminophenol in high yield by reductive alkylation while inhibiting an undesired condensation reaction forming heavy matter even when a catalyst for reduction is repeatedly used, which process causes no serious corrosion of equipment and can be embodied on an industrial scale.

As a result of extensive investigations, the present inventors have found that the above object of this invention is accomplished by conducting reductive alkylation while continuously adding an organic carboxylic acid into the reaction system, thus producing the present invention.

That is, the present invention relates to a process for preparing an N-alkyl-substituted aminophenol, which comprises continuously feeding an aldehyde or a ketone to a reaction system containing an organic solvent, a catalyst for reduction, hydrogen, and an aminophenol to conduct a reductive alkylation reaction, wherein said reductive alkylation reaction is carried out while continuously adding an organic carboxylic acid into the reaction system.

DETAILED DESCRIPTION OF THE INVENTION

Aminophenols which can be used in the present invention include o-aminophenol, m-aminophenol, and p-aminophenol.

Aldehydes which can be used in the present invention include aliphatic aldehydes, e.g., formaldehyde, acetaldehyde, propionaldehyde, butyraldehyde, and isoamylaldehyde; cyclic aldehydes, e.g., cyclohexylaldehyde and furfural; and aromatic aldehydes, e.g., benzaldehyde and p-tolualdehyde.

Ketones which can be used in the present invention include aliphatic ketones, e.g., acetone, 2-butanone, and 4-methyl-2-pentanone; cyclic ketones, e.g., cyclopentanone and cyclohexanone; and aromatic ketones, e.g., acetophenone and p-methylacetophenone.

N-Alkyl-substituted aminophenols which can be prepared by the process of this invention include N-monoalkylaminophenols, e.g., N-ethylaminophenol, N-propylaminophenol, N-butylaminophenol, N-cyclohexylaminophenol, N-benzylaminophenol, and N-isopropylaminophenol; and N,N-dialkylaminophenols, e.g., N,N-diethylaminophenol, N,N-dibutylaminophenol, N-ethyl-N-isobutylaminophenol, and N-ethyl-N-isoamylaminophenol.

The reductive alkylation reaction between an aminophenol and an aldehyde or a ketone can be carried out by continuously feeding an aldehyde or a ketone to a system containing an organic solvent, a catalyst for reduction, hydrogen, and an aminophenol.

Examples of suitable organic solvents which can be used include aliphatic alcohols, e.g., methanol and ethanol.

The catalyst for reduction which can be used is a catalyst capable of catalyzing reductive alkylation, such as platinum, palladium, and nickel. Platinum and/or palladium-on-carbon is particularly preferred. If desired, in order to conduct the reaction in a stable manner, a loss of the catalyst due to size reduction or filtration for recovering may be made up by addition of a small amount of fresh catalyst to the next reaction system.

The greatest characteristic feature of the present invention lies in that an organic carboxylic acid is continuously added to the reductive alkylation reaction system. In the reductive alkylation reaction of the aminophenol, there is generally an induction period of several minutes between the contact of the aminophenol with the aldehyde or ketone and the actual commencement of the reaction. On the other hand, upon contact between the aminophenol and the aldehyde or ketone, there is observed a relatively rapid reaction to form a Schiff base and then to form heavy matter. Therefore, if the reaction forming a heavy matter proceeds during the induction period, the catalyst activity is inhibited by the formed heavy matter, which leads to reduction in yield of the desired N-alkylaminophenol.

According to the present invention, the formation of a heavy matter can be controlled by continuous addition of an organic carboxylic acid to the reaction system.

Organic carboxylic acids which can be used in the present invention include monocarboxylic acids having from 1 to carbon atoms, dicarboxylic acids having from 2 to 8 carbon atoms, and hydroxycarboxylic acids having from 1 to 8 carbon atoms. Examples of suitable monocarboxylic acids are acetic acid, propionic acid, butyric acid, isobutyric acid, valeric acid, isovaleric acid, and benzoic acid. Examples of suitable dicarboxylic acids are oxalic acid, malonic acid, succinic acid, maleic acid, and isophthalic acid. Examples of suitable hydroxycarboxylic acids are glycolic acid, lactic acid, malic acid, tartaric acid, and citric acid. Particularly preferred of them are acetic acid, propionic acid, butyric acid, isobutyric acid, isovaleric acid, and oxalic acid. These organic carboxylic acids may be used either individually or in combination of two or more thereof.

The organic carboxylic acid, added in a small amount, is usually used as diluted with an organic solvent which is used for the reaction. A total amount of the organic carboxylic acid to be added ranges usually from 0.05 to 5% by weight, and preferably from 0.2 to 2% by weight, based on the amount of the charged aminophenol. If it is less than 0.05% by weight, the effect produced is small, particularly in the preparation of N,N-dialkylaminophenols. If it exceeds 5% by weight, the rate of reaction is increased, but the formation of heavy matter is ready to occur to cause reduction in yield of the desired product.

The reductive alkylation reaction according to the present invention is effected by continuously feeding the aldehyde or ketone to the reaction system comprising an aminophenol, an organic solvent, and a catalyst for reduction. The reaction is usually carried out at a temperature of from normal temperature to 150° C. under a hydrogen pressure of from 2 to 30 kg/cm$^2$G.

The ratio of the aminophenol to the aldehyde or ketone (total amount) is not particularly limited but generally ranges from 1:1.05 to 1:4 by mole.

The amount of the catalyst for reduction is not particularly limited but usually ranges from 0.5 to 10% based on the amount of the charged aminophenol.

Continuous addition of the organic carboxylic acid is conducted over the whole reaction period or a part of the reaction period. In a preferred embodiment, continuous addition of the aldehyde or ketone to the reaction system containing an organic solvent, a catalyst for reduction, hydrogen, and an aminophenol is started and, then, after confirming the commencement of a reductive alkylation reaction by observation of hydrogen absorption, continuous addition of the organic carboxylic acid is started. In the most preferred embodiment, the addition of an organic carboxylic acid is started at least 10 minutes after the start of the aldehyde or ketone feeding, and completed before the completion of the addition of a prescribed amount of the aldehyde or ketone. The above-described mode of addition is particularly effective in cases where the catalyst for reduction is repeatedly used.

The terminology "continuous addition" of the organic carboxylic acid not only literally means continuous addition but includes appropriately designed intermittent addition as far as such a mode of addition does not deviate from the concept of the present invention.

The present invention is now illustrated in greater detail with reference to Examples and Comparative Examples, but it should be understood that the present invention is not deemed to be limited thereto. All the parts, percents and ratios are by weight unless otherwise specified.

EXAMPLE 1

In a 5 l-volume SUS-made autoclave equipped with a stirrer were charged 1,091 g of a methanol solution containing 25% of m-aminophenol and 745 g of a methanol slurry containing 17.7 g of a catalyst for reduction (5% platinum-on-carbon) which had been spent once in a reductive alkylation reaction and recovered. The atmosphere in the autoclave was displaced first with nitrogen and then with hydrogen, and the hydrogen pressure was raised up to 10 kg/cm$^2$G. While maintaining the hydrogen pressure constant, 563 g of a methanol solution containing 45% of acetaldehyde was fed to the reaction system at such a constant rate that the feed could be completed in 55 minutes. After hydrogen absorption was confirmed and 15 minutes after the start of the feed of the methanol solution of acetaldehyde, 16.4 g of a methanol solution containing 10% of acetic acid was started to be continuously added at a constant rate over a period of 15 minutes. During the addition, the reaction heat was removed so as to control the reaction temperature not to exceed 42° C. After completion of the aldehyde feed, the reaction system was kept at 40°±2° C. for 2.5 hours to complete the reductive alkylation reaction. After the reaction, the reaction mixture was cooled, the pressure was released, and the catalyst was removed by filtration. The reaction mixture thus recovered was analyzed by gas chromatography (GC), liquid chromatography (LC) and gel-permeation chromatography (GPC) and, as a result, revealed satisfactory reaction results: yield of N,N-diethyl-m-aminophenol=94.6% (by mole, based on charged m-aminophenol; hereinafter the same); yield of N-ethyl-m-aminophenol=0.6%; yield of heavy matter=3.1%.

COMPARATIVE EXAMPLE 1

A reductive alkylation reaction was carried out in the same manner as in Example 1, except that the whole amount of the 10% methanol solution of acetic acid was added all at once simultaneously with the addition of the 25% methanol solution of m-aminophenol. Analyses by GC, LC, and GPC revealed unsatisfactory reaction results: yield of N,N-diethyl-m-aminophenol=81.6%; yield of N-ethyl-m-aminophenol=2.3%; yield of heavy matter=12.6%.

EXAMPLES 2 TO 4 AND COMPARATIVE EXAMPLES 2 TO 3

Examination on various amounts of acetic acid was made according to the procedures of Example 1. Acetic acid was added as a 10% solution in methanol. The results of analyses inclusive of those obtained in Example 1 are shown in Table 1 below.

TABLE 1

| Example No. | Amount of Acetic Acid (wt %)* | Yield of Products (mol %)** | | |
|---|---|---|---|---|
| | | N,N-Diethyl-m-amino-phenol | N-Ethyl-m-amino-phenol | Heavy Matter |
| Comparative Example 2 | — | 84.6 | 9.3 | 3.4 |
| Example 2 | 0.2 | 93.7 | 1.2 | 3.1 |
| Example 1 | 0.6 | 94.6 | 0.6 | 3.1 |
| Example 3 | 1 | 94.0 | 0.2 | 4.2 |
| Example 4 | 2 | 92.4 | 0.0 | 5.1 |
| Comparative Example 3 | 10 | 87.5 | 0.0 | 8.4 |

Note:
*: Based on charged m-aminophenol.
**: Based on charged m-aminophenol.

EXAMPLE 5

A reductive alkylation reaction was carried out in the same manner as in Example 1, except that the addition of acetic acid was started 10 minutes after the start of the addition of acetaldehyde and continued for 40 minutes. Analyses by GC, LC, and GPC revealed satisfactory reaction results: yield of N,N-diethyl-m-aminophenol=94.5%; yield of N-ethyl-m-aminophenol=0.7%; yield of heavy matter=2.9%.

EXAMPLES 6 TO 8

Examination on various organic carboxylic acids in place of acetic acid was made according to the procedures of Example 1. Each organic carboxylic acid was added as a 10% solution in methanol. The results of analyses are shown in Table 2 below.

TABLE 2

| Example No. | Organic Carboxylic Acid | | Yield of Products (mol %)** | | |
|---|---|---|---|---|---|
| | Kind | Amount (wt %)* | N,N-Diethyl-m-Amino-phenol | N-Ethyl-mAmino-phenol | Heavy Matter |
| 6 | propionic acid | 0.8 | 93.5 | 0.5 | 3.3 |
| 7 | butyric acid | 1.0 | 92.9 | 0.5 | 3.8 |
| 8 | oxalic acid | 0.4 | 94.5 | 0.2 | 3.6 |

Note:
*: Based on charged m-aminophenol.
**: Based on charged m-aminophenol.

EXAMPLE 9

A reductive alkylation reaction was carried out to synthesize N,N-dibutyl-m-aminophenol in the same manner as in Example 1, except that 901 g of a methanol solution containing 50% of n-butyraldehyde was used in place of 563 g of the 45% methanol solution of acetaldehyde and fed over a period of 60 minutes.

The reaction results were satisfactory: yield of N,N-dibutyl-m-aminophenol=94.1%; yield of N-butyl-m-aminophenol=1.8%; yield of heavy matter=2.5%.

EXAMPLE 10

A reductive alkylation reaction was carried out to synthesize N-cyclohexyl-m-aminophenol in the same manner as in Example 1, except that 589 g of a methanol solution containing 50% of cyclohexanone was used in place of 563 g of the 45% methanol solution of acetaldehyde and fed over a period of 60 minutes.

As a result, the yield of N-cyclohexyl-m-aminophenol was 96.2%, and the yield of heavy matter was 2.1%.

EXAMPLE 11

N-Ethyl-N-isobutyl-m-aminophenol was synthesized in the same manner as in Example 1 as follows.

In a 5 l-volume SUS-made autoclave equipped with a stirrer were charged 1091 g of a methanol solution containing 25% of m-aminophenol and 745 g of a methanol slurry containing 17.7 g of a catalyst for reduction (5% platinum-on-carbon) which had been spent once for a reaction and recovered. The atmosphere in the autoclave was displaced first with nitrogen and then with hydrogen, and the hydrogen pressure was raised up to 10 kg/cm$^2$G. While maintaining the hydrogen pressure constant, 397 g of a methanol solution containing 50% of isobutylaldehyde was fed to the reaction system at such a constant rate that the feed could be completed in 25 minutes. After hydrogen absorption was confirmed and 10 minutes after the start of the feeding of the methanol solution of isobutyl-aldehyde, 16.4 g of a methanol solution containing 10% of acetic acid was continuously added at a constant rate over a period of 15 minutes. After the addition of isobutylaldehyde, the reaction mixture was aged for 50 minutes. Then, 343 g of a methanol solution containing 45% of acetaldehyde was continuously fed over a period of 35 minutes to conduct N-ethylation. The reaction mixture was aged for 60 minutes to complete reductive alkylation. During the reaction, the reaction heat was removed so as to control the reaction temperature not to exceed 42° C. After completion of the reaction, the reaction mixture was cooled, the pressure was released, and the catalyst was removed by filtration. The results of analyses revealed satisfactory reaction results: yield of N-ethyl-N-isobutyl-m-aminophenol=92.8%; yield of heavy matter=2.8%.

EXAMPLE 12

N-Ethyl-N-isoamyl-m-aminophenol was synthesized by reductive alkylation in the same manner as in Example 11, except for replacing 397 g of the 50% methanol solution of isobutylaldehyde with 474 g of a methanol solution containing 50% of isoamylaldehyde.

The yield of N-ethyl-N-isoamyl-m-aminophenol was 92.5%, and the yield of a heavy matter was 2.7%.

As described and demonstrated above, according to the present invention, there is provided a process for preparing N-alkyl-substituted aminophenols which achieves high yields while inhibiting unfavorable reaction forming a heavy matter even by repeatedly reusing catalyst for reduction. The process does not cause serious corrosion of materials and can be industrialized.

While the invention has been described in detail and with reference to specific embodiments thereof, it will be apparent to one skilled in the art that various changes and modifications can be made therein without departing from the spirit and scope thereof.

What is claimed is:

1. A process for preparing an N-alkyl-substituted aminophenol, which comprises continuously feeding an aldehyde or a ketone to a reaction system containing an organic solvent, a catalyst for reduction, hydrogen, and an aminophenol to conduct a reductive alkylation reaction, wherein said reductive alkylation reaction is carried out while continuously adding an organic carboxylic acid into the reaction system, and wherein said organic carboxylic acid is added in a total amount of from 0.05 to 5% by weight based on the aminophenol.

2. A process as claimed in claim 1, wherein the continuous addition of said organic carboxylic acid is started after at least 10 minutes after the start of the continuous feed of the aldehyde or ketone.

3. A process as claimed in claim 1, wherein said organic carboxylic acid is at least one of monocarboxylic acids having from 1 to 8 carbon atoms, dicarboxylic acids having from 2 to 8 carbon atoms, and hydroxycarboxylic acids having from 1 to 8 carbon atoms.

4. A process as claimed in claim 2, wherein said organic carboxylic acid is at least one of monocarboxylic acids having from 1 to 8 carbon atoms, dicarboxylic acids having from 2 to 8 carbon atoms, and hydroxycarboxylic acids having from 1 to 8 carbon atoms.

* * * * *